United States Patent [19]

Demers

[11] Patent Number: 5,629,178
[45] Date of Patent: May 13, 1997

[54] METHOD FOR ENHANCING AMPLIFICATION IN THE POLYMERASE CHAIN REACTION EMPLOYING PEPTIDE NUCLEIC ACID (PNA)

[75] Inventor: Daniel B. Demers, Broad Run, Va.

[73] Assignee: Genetics & IVF Institute, Fairfax, Va.

[21] Appl. No.: 330,790

[22] Filed: Oct. 28, 1994

[51] Int. Cl.$^6$ .............................. C12P 19/34; C12Q 1/70; C12Q 1/68; C07H 21/04
[52] U.S. Cl. ................................ 435/91.2; 435/5; 435/6; 536/24.5; 514/44
[58] Field of Search ................................. 435/6, 5, 91.2; 530/300; 536/24.5; 514/44

[56] References Cited

FOREIGN PATENT DOCUMENTS

WO9220702  11/1992  WIPO.
WO9220703  11/1992  WIPO.

OTHER PUBLICATIONS

Peter E. Nielsen, et al., "Sequence specific inhibition of DNA restriction enzyme cleavage by PNA", Nucleic Acids Research, 1993, vol. 21, No. 2 197–200.
Michael Egholm, et al., "Peptide Nucleic Acids (PNA). Oligonucleotide Analogues with an Achiral Peptide Backbone", J. Am. Chem. Soc. 1992, 114, 1895–1897.
Seog K. Kim, et al., "Right-Handed Triplex Formed between Peptide Nucleic Acid PNA-$T_8$ and Poly(dA) Shown by Linear and Circular Dichroism Spectroscopy", J. Am. Chem. Soc. 1993, 115, 6477–6481.
Michael Egholm, et al., "Peptide Nucleic Acids containing Adenine or Guanine recognize Thymine and Cytosine in Complementary DNA Sequences", J. Chem. Soc. Chem. Comm., 1993, 800–801.
Kim L. Deuholm, et al., "An Efficient Synthesis of Boc–Aminoacetaldehyde and its Application to the Synthesis of N-(2-BOC-Aminoethyl)Glycine Esters", Organic Preparations and Procedures Int., 25(4), 457–461 (1993).

Vadim Demidov, et al., "Sequence selective double strand DNA cleavage by Peptide Nucleic Acid (PNA) targeting using nuclease S1", Nucleic Acids Research, 1993, vol. 21, No. 9, 2103–2107.
Dmitry Y. Cherny, et al., "DNA unwinding upon strand–displacement binding of a thymine–substituted polyamide to double–stranded DNA", Proc. Natl. Acad. Sci. USA, vol. 90, pp. 1667–1670, Mar. 1993.
Birgitte Hyrup, et al., "Modification of the Binding Affinity of Peptide Nucleic Acids (PNA). PNA with Extended Backbones consisting of 2–Aminoethyl–β–alanine or 3–Aminopropylglycine Units", J. Chem. Soc. Commun. 1993, 518–519.
Michael Egholm, et al., "PNA hybridizes to complementary oligonucleotides obeying the Watson–Crick hydrogen–bonding rules", Nature, vol. 365, 566, 7 Oct. 1993.
Jeffery C. Hanvey, et al., "Antisense and Antigene Properties of Peptide Nucleic Acids", Science, vol. 258, 1481, 27 Nov. 1992.
Peter E. Nielsen, et al., "Peptide nucleic acids (PNAs): Potential anti–sense and anti–gene agents", Anti–Cancer Drug Design (1993), 8, 53–63.
Saiki, In PCR Protocols: A Guide to Methods and Apppplications, Academic Press, 1990, pp. 13–20.
WO94/28171, PNA Diagnostics, Stanley, Nucleic Acid Analog Assay Procedures., 8 Dec. 1994.
Drum et al., Nucleic Acids Research 21:5332–5336,. 1993.

*Primary Examiner*—W. Gary Jones
*Assistant Examiner*—Dianne Rees
*Attorney, Agent, or Firm*—McDermott, Will & Emery

[57] ABSTRACT

A process for producing a particular nucleic acid sequence from a given sequence of DNA or RNA in amounts which are large compared to the amount initially present, using PNAs in conjunction with the polymerase chain reaction (PCR) is disclosed.

118 Claims, 6 Drawing Sheets

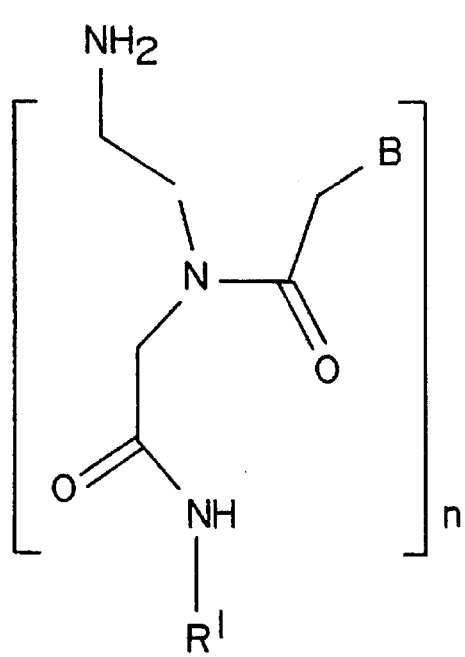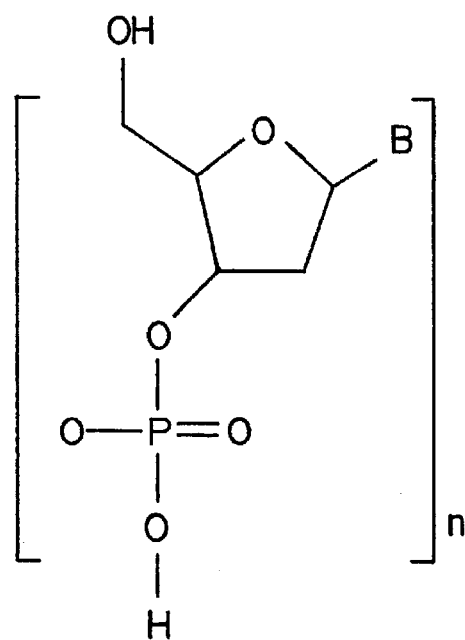
PNA
FIG. 2A
DNA
FIG. 2B

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( x i ) SEQUENCE DESCRIPTION: SEQ ID NO:1:

CAGTATCCGA  10

( 2 ) INFORMATION FOR SEQ ID NO:2:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( x i ) SEQUENCE DESCRIPTION: SEQ ID NO:2:

CAGGATCCGA  10

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:3:

```
CGAAGCTTCA GTATCCGA                                         18
```

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:4:

```
GAAACTGGCC TCCAAACACT CCCCGCCG                              28
```

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:5:

```
GTCTTGTTGG AGATGCACGT GCCCCTTGC                             29
```

METHOD FOR ENHANCING AMPLIFICATION IN THE POLYMERASE CHAIN REACTION EMPLOYING PEPTIDE NUCLEIC ACID (PNA)

BACKGROUND OF THE INVENTION

The present invention relates to a process for amplifying nucleic acid sequences present in a sample. More specifically, the present invention relates to a method of employing peptide nucleic acids (PNA) to enhance the amplification of nucleic acid sequences via the polymerase chain reaction. Still more specifically, the present invention relates to a process for producing a particular nucleic acid sequence from a given sequence of DNA or RNA in amounts which are large compared to the amount initially present, using PNAs in conjunction with the polymerase chain reaction (PCR).

The polymerase chain reaction has, since its conception in April 1983, become a standard technique for amplification of nucleic acid sequences. In this process one or more specific nucleic acid sequences present in a nucleic acid or mixture thereof are amplified using primers and agents for polymerization and then detecting the amplified sequence. The extension product of one primer, when hybridized to the other, becomes a template for the production of the desired specific nucleic acid sequence, and vice versa, and the process is repeated as often as is necessary to produce the desired amount of the sequence.

The DNA or RNA may be single- or double-stranded, and may be a relatively pure species or a component of a mixture of nucleic acids. The PCR process utilizes a repetitive reaction to accomplish the amplification of the desired nucleic acid sequence. Indeed, in the approximately ten years since its discovery, the PCR technique has been widely employed in the field of molecular biology in detecting and identifying nucleic acid sequences. For example, the polymerase chain reaction (PCR) has been extensively used to amplify DNA loci in genome mapping, linkage studies, genetic diagnostics, forensics, and paternity testing. The widespread use of this technique is testimony to the utility of the process.

Unfortunately, the polymerase chain reaction is not without problems. The PCR process depends upon multiple steps of annealing and melting (separation of two complementary strands). Under ideal conditions, one can envision the separation of the two complementary strands of double-stranded DNA, annealing of the complementary primers, and elongation of the primers with a polymerase to produce two molecules of double-stranded DNA. This cycle is repeated while the quantity of the desired sequence grows exponentially.

However, in most contexts in which the polymerase chain reaction is employed, situations are less than ideal. Often DNA of interest to the biotechnological community contains a number of repeat or near-repeat sequences. Additionally, nucleic acid sequences frequently contain a number of internally self-complementary sequences. These repeating and self-complementary sequences increase the likelihood that the nucleic acid sequence will experience interstrand and intrastrand interactions, possibly resulting in a nucleic acid strand folding in upon itself.

Further, as the polymerase chain reaction progresses, the concentration of complementary DNA sequences increases exponentially, while the concentration of primer commonly remains constant or decreases. This can result in the product of the interim cycles of the polymerase chain reaction successfully competing with the primers required for the next cycle of elongation. Such competition can significantly reduce the efficiency and yield of the polymerase chain reaction.

Moreover, diploid DNA poses additional challenges. Robust amplification of allelic sequences is often difficult, particularly when there is a significant size difference between the two alleles. Smaller alleles simply amplify more efficiently. This phenomenon, known as differential amplification, results in the generation of more copies of the smaller allele and thus a more intense band on the subsequent electrophoresis gel. At best, the larger allele is underrepresented relative to the smaller allele, at worst, differential amplification can result in allelic dropout, in which the larger allele amplifies so poorly relative to the smaller allele that the larger allele can neither be visualized nor detected. Differential amplification and allelic dropout can complicate genetic analyses.

The terms "peptide nucleic acid" and "PNA" refer to a DNA analog with a backbone consisting of N-(2-aminoethyl)glycine units. To this backbone, analogous to DNA, are attached the nucleobases—for DNA, adenine, guanine, cytidine, and thymine. The individual monomeric units of PNA can be synthesized to furnish a PNA chain having a specific sequence of bases. The synthesis of such PNA chains is detailed in various publications, including Science 254, 1497 (1991); J. Am. Chem. Soc. 114, 9677 (1992); J. Am. Chem. Soc. 144, 1895 (1992); J. Chem. Soc. Chem. Comm. 800 (1993); Proc. Nat. Acad. Sci. USA 90, 1667 (1993); Intercept Ltd. 325 (1992); J. Am. Chem. Soc. 114, 9677 (1992); Nucleic Acids Res. 21, 197 (1993); J. Chem. Soc. Chem. Commun. 518 (1993); Anti-Cancer Drug Design 8, 53 (1993); Nucleic Acids Res. 21, 2103 (1993); Org. Proc. Prep. 25, 457 (1993); CRC Press 363 (1992); J. Chem. Soc. Chem. Commun. 800 (1993); J. Am. Chem. Soc. 115, 6477 (1993); Nature 365, 566 (1993); ABRF News Vol. 4, No. 3 (1993); Science 258, 1481 (1992); WO 8-92/20702; and WO 92/20703, the contents of which are incorporated herein by reference. Additionally, specific sequences of PNA are commercially available from BioSearch Div., PerSeptive Biosystems, Inc., Bedford, Mass.

PNA has been demonstrated to be a potent DNA mimic in terms of sequence-specific annealing. Experimental results (discussed in the above publications) have demonstrated that at physiological ionic strength a PNA/DNA duplex is generally 1° C. per base pair more stable thermally than the corresponding DNA/DNA duplex. Other experimental data has indicated that PNA is more stable in the cell than DNA; that PNA binds to DNA or RNA 50–100 times more tightly than either DNA or RNA; that PNA can invade and displace double-stranded DNA (dsDNA); and that the backbone of PNA adopts a helical conformation. However, a single base mismatch in a PNA/DNA duplex is much more destablizing than a mismatch in the corresponding DNA/DNA duplex. Furthermore, PNA does not function as a primer for DNA polymerase.

Recently, PNAs have been used to detect single base mutations through PCR clamping. In Nucleic Acids Research 21, 5332 (1993), PNAs were reported to form a PNA/DNA complex which effectively blocked the formation of a PCR product. However, this PNA-directed PCR clamping results in a blocking of PCR amplification, rather than an enhancement of the polymerase chain reaction.

Accordingly, there remains a need for an efficient and effective method of amplifying existing nucleic acid sequences present in a sample using the polymerase chain reaction.

SUMMARY OF THE INVENTION

Accordingly, an object of the present invention is to provide a method for enhancing amplification of nucleic acid sequences using the polymerase chain reaction.

Another object of the present invention is to provide a kit for detecting a nucleic acid sequence of interest.

Still another object of the present invention is to provide a method of cloning into a vector a nucleic acid sequence of interest.

Still another object of the present invention is to provide an amplified nucleic acid sequence.

Still another object of the present invention is to provide a method for replicating a target nucleic acid strand with a polymerase to produce a complementary nucleic acid strand.

Still another object of the present invention is to provide a method for replicating a target nucleic acid strand with a thermostable DNA polymerase to produce a complementary nucleic acid strand.

Still another object of the present invention is to provide a method for replicating a target nucleic acid strand with a polymerase.

These and other objects of the present invention are achieved by means of a process for detecting the presence or absence of at least one nucleic acid sequence of interest in a sample containing a nucleic acid or a mixture of nucleic acids, comprising treating the sample with at least one PNA oligomer which binds within the region of nucleic acid to be amplified. More specifically, the present invention resides in a process for amplifying one or more specific nucleic acid sequences present in a nucleic acid or mixture thereof using oligonucleotide primers and an agent for polymerization, employing at least one PNA oligomer to reduce the incidence of interstrand and intrastrand interactions, and then isolating and/or detecting the amplified sequence. This method is expected to be more efficient and effective than the conventional PCR technique for producing large amounts of nucleic acid from a target sequence, especially with DNA or RNA that contains one or more repeat or near-repeat sequences.

More specifically, the present invention provides a process for detecting the presence or absence of at least one nucleic acid sequence of interest in a sample containing a nucleic acid or mixture of nucleic acids, wherein the sample is suspected of containing said sequence or sequences, which process comprises the steps of treating the sample with at least one PNA oligomer which binds within the nucleic acid sequence to be amplified; and polymerizing a nucleic acid sequence which is complementary to the nucleic acid sequence of interest.

In another preferred embodiment of the present invention, a method of amplifying a nucleic acid sequence of interest in a sample containing at least one nucleic acid, comprises: (a) treating the sample with (i) an agent for polymerization, (ii) at least one oligonucleotide primer which binds to a strand of each different nucleic acid sequence of interest, (iii) at least one PNA oligomer which is substantially complementary to a portion of and which binds within the nucleic acid sequence of interest at a position different from the position at which the oligonucleotide primer binds, and (iv) four different nucleoside triphosphates, forming a first mixture; (b) heating the first mixture to within a first temperature range so as to denature the nucleic acid and to separate any of the at least one oligonucleotide primer and any of the at least one PNA oligomer which is bound to the nucleic acid, forming a second mixture; (c) cooling the second mixture to within a second temperature range at which the at least one PNA oligomer binds to the nucleic acid sequence of interest, forming a third mixture; (d) bringing the third mixture to within a third temperature range at which the at least one oligonucleotide primer binds to the nucleic acid sequence of interest and at which an extension product is synthesized from the oligonucleotide primer on each strand, provided the nucleic acid sequence of interest is present, said synthesis employing the nucleic acid as a template, and whereby the at least one PNA oligomer is displaced from the nucleic acid sequence of interest during said synthesis.

In still another preferred embodiment, the present invention relates to a kit for detecting at least one nucleic acid sequence of interest in a sample, comprising: (a) a container containing at least one oligonucleotide primer for each strand of each nucleic acid sequence of interest, each of said at least one oligonucleotide primer being substantially complementary to a strand of each nucleic acid sequence of interest; (b) a container containing at least one PNA oligomer which is substantially complementary to a portion of and which binds within each nucleic acid sequence of interest at a position different from the position at which the at least one oligonucleotide primer binds; and (c) a container containing each of four different nucleoside triphosphates.

In still another preferred embodiment, the present invention pertains to a process for cloning into a vector a nucleic acid sequence of interest in a sample containing at least one nucleic acid, comprising: (a) treating the sample with (i) an agent for polymerization, (ii) at least one oligonucleotide primer containing a restriction site at its 5' end and which is substantially complementary to and binds to a strand of each different nucleic acid sequence of interest, (iii) at least one PNA oligomer which is substantially complementary to a portion of and which binds within the nucleic acid sequence of interest at a position different from the position at which the oligonucleotide primer binds, and (iv) four different nucleoside triphosphates, forming a first mixture; (b) heating the first mixture to within a first temperature range so as to denature the nucleic acid and to separate any of the at least one oligonucleotide primer and any of the at least one PNA oligomer which is bound to the nucleic acid, forming a second mixture; (c) cooling the second mixture to within a second temperature range at which the at least one PNA oligomer binds to the nucleic acid, forming a third mixture; (d) bringing the third mixture to within a third temperature range at which the at least one oligonucleotide primer binds to the nucleic acid sequence of interest and at which an extension product is synthesized from the oligonucleotide primer on each strand, provided the nucleic acid sequence of interest is present, said synthesis employing the nucleic acid as a template, and whereby the at least one PNA oligomer is displaced from the nucleic acid sequence of interest during said synthesis (e) adding to the product of step (d) a restriction enzyme which cleaves at said restriction site to thereby obtain cleaved products; and (f) ligating the cleaved products into at least one cloning vector.

The steps detailed above may be repeated until the desired level of sequence amplification is obtained.

In still another preferred embodiment, the present invention pertains to a method for replicating a target nucleic acid strand with a polymerase to produce a complementary nucleic acid strand, comprising:(A) providing a peptide nucleic acid (PNA) which, (1) is substantially complementary in sequence to nucleobases in at least a portion of the target strand, (2) anneals with said portion of the target strand, and (3) when annealed with said portion of the target strand, does not serve as a replication initiation site for the polymerase; and (B) annealing the PNA to the target strand prior to initiating replication thereby to enhance replication by the polymerase during production of the complementary nucleic acid strand.

In still another preferred embodiment, the present invention pertains to a method for replicating a target nucleic acid strand with a thermostable DNA polymerase to produce a complementary nucleic acid strand, comprising: (A) providing a peptide nucleic acid (PNA) which, (1) is substantially complementary in sequence to nucleobases in at least a portion of the target strand, (2) anneals with said portion of the target strand, and (3) when annealed with said portion of the target strand, does not serve as a replication initiation site for the polymerase; and (B) annealing the PNA to the target strand prior to initiating replication by the polymerase thereby to enhance replication by the polymerase during production of the complementary nucleic acid strand.

In still another preferred embodiment, the present invention pertains to a method for replicating a target nucleic acid strand with a polymerase comprising: (A) providing a target nucleic acid strand having a multiplicity of nucleobase sequence repeats; (B) annealing a PNA to the target strand which: (1) is substantially complementary in sequence to at least a portion of one of the repeats; (2) anneals with the at least a portion of one of the repeats thereby to form a target strand-PNA complex; and (3) when annealed with the at least a portion of one of the repeats, does not serve as a replication initiation site for the polymerase; and (C) incubating the complex in the presence of a polymerase, such that the polymerase enhances replication of the target strand as compared with when the target strand is not complexed with the PNA.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 2 (A and B) illustrates the chemical structure of the monomeric subunits of PNA and deoxyribonucleic acid (DNA), where B is the nucleobase and $R^1$ is either a hydrogen atom or lysine amide.

DETAILED DESCRIPTION OF THE PREFERRED EMBODIMENTS

In an attempt to enhance the amplification of nucleic acid sequences using the polymerase chain reaction, the program of research directed to diminishing the interstrand and intrastrand interactions which decrease the efficiency of the PCR reaction was undertaken. That investigation resulted in the discovery that PNA oligomers, which are substantially complementary to a portion of the nucleic acid sequence of interest but different from that portion of the nucleic acid sequence to which the oligonucleotide primers bind, apparently sufficiently block the nucleic acid functioning as a template, such that the template is unavailable for interactions, either interstrand or intrastrand, while allowing amplification of the sequence to proceed.

The proposed mechanism will become apparent in the following exemplary comparison of the conventional polymerase chain reaction and the PNA-enhanced PCR reaction.

Figure 1:
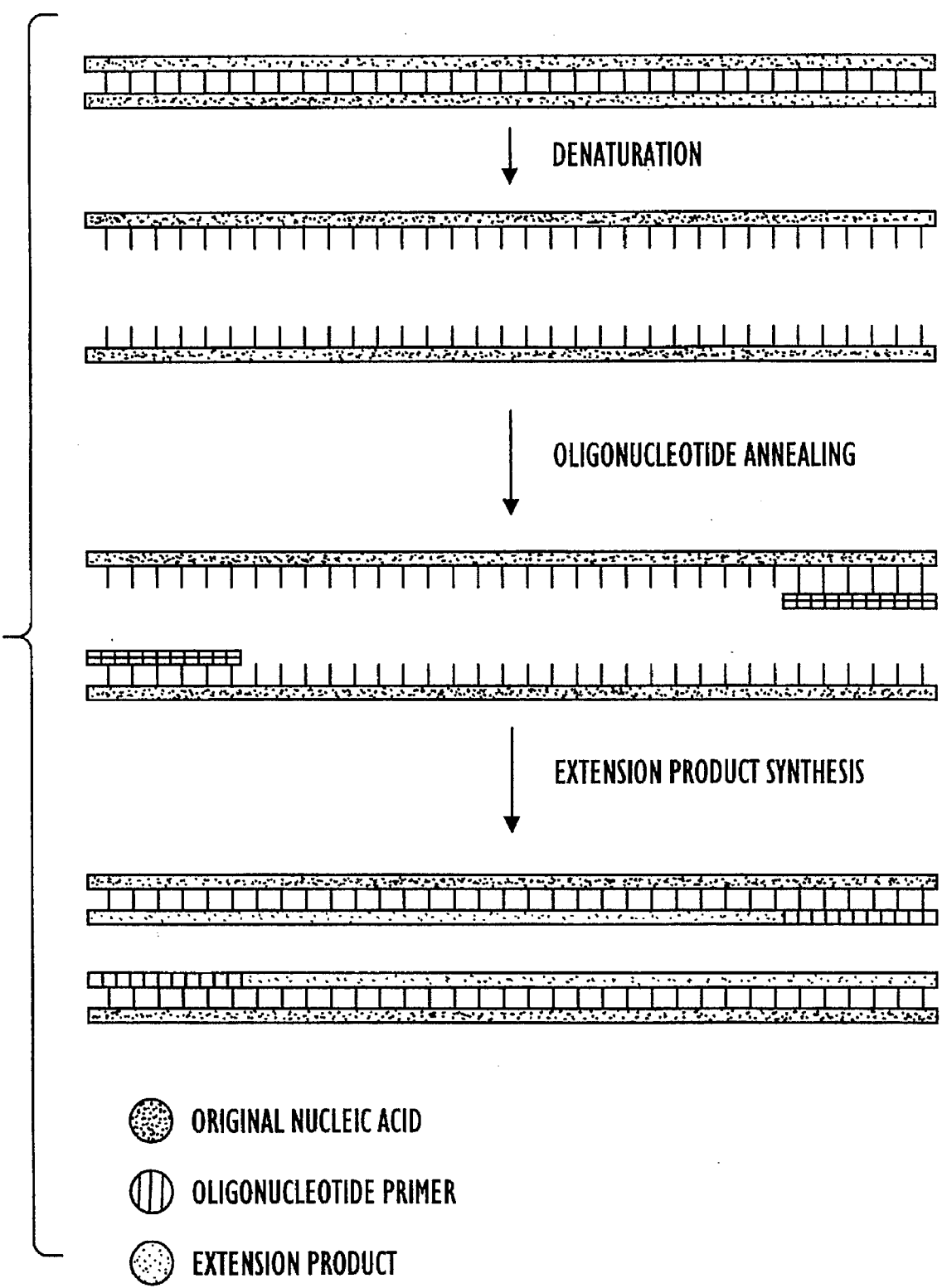
FIG. 1 provides a schematic illustration of the conventional polymerase chain reaction.
Figures 3A, 3B:
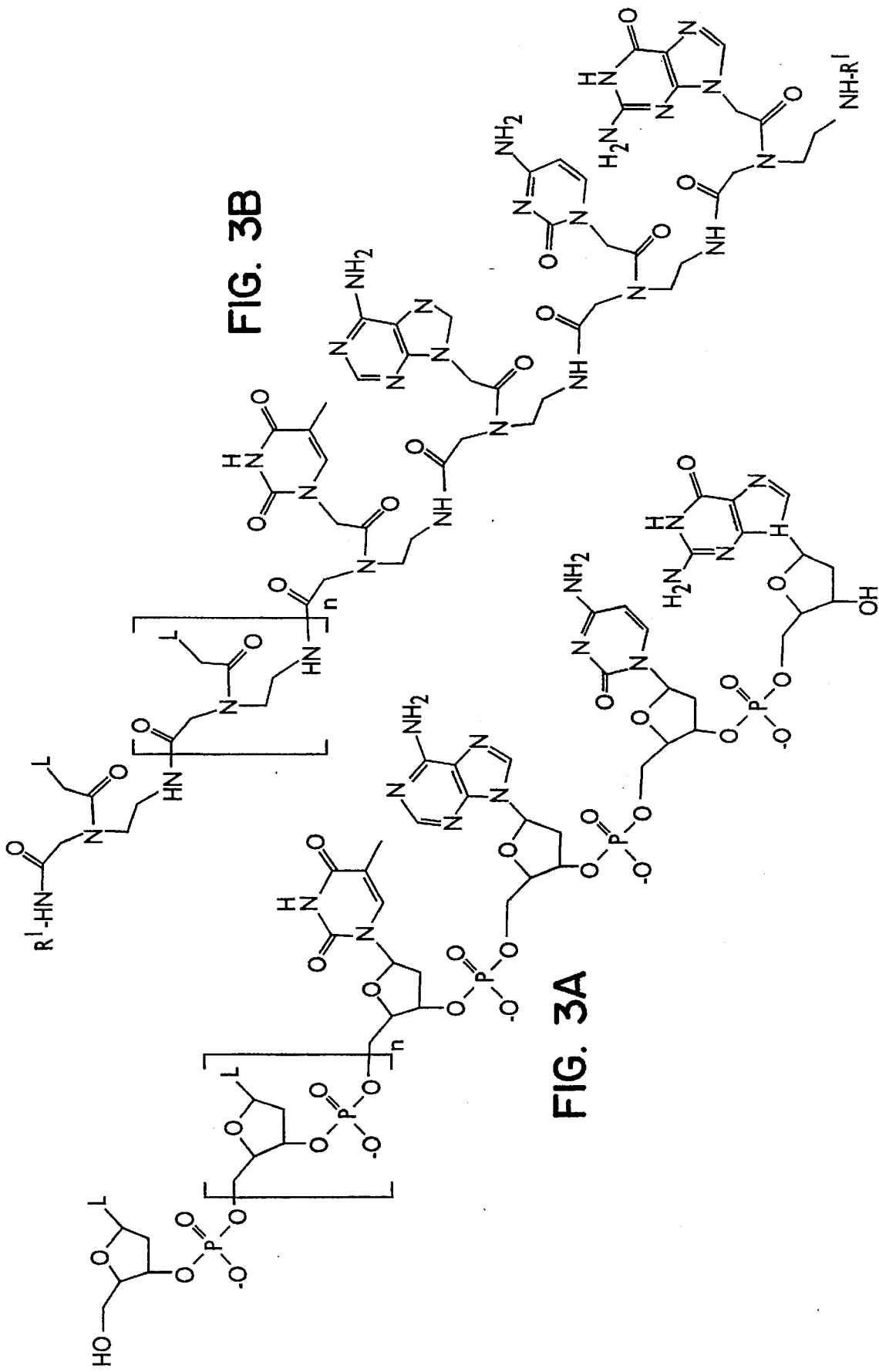
FIG. 3 (A and B) shows a naturally occurring deoxyribooligonucleotide oligomer (A) and PNA oligomer (B).

In the conventional PCR reaction, as illustrated in FIG. 1, a double-stranded DNA molecule, for example, containing the desired sequence comprised of complementary strands is utilized as the nucleic acid. The first and each subsequent reaction cycle extension of each oligonucleotide primer on the original template will produce one new ssDNA molecule product of indefinite length which terminates with only one of the primers. These products, referred to as "long products," will accumulate in a linear fashion; that is, the amount present after any number of cycles will be proportional to the number of cycles.

The long products thus produced will act as templates for one or the other of the oligonucleotide primers and the at least one PNA oligomer during subsequent cycles and will produce molecules of the desired sequence. These molecules will also function as templates for one or the other of the oligonucleotide primers and the at least one PNA oligomer, producing additional amounts of the desired sequence. Thus a chain reaction can be sustained which will result in the accumulation of the desired sequence at an exponential rate relative to the number of cycles.

Figure 4:
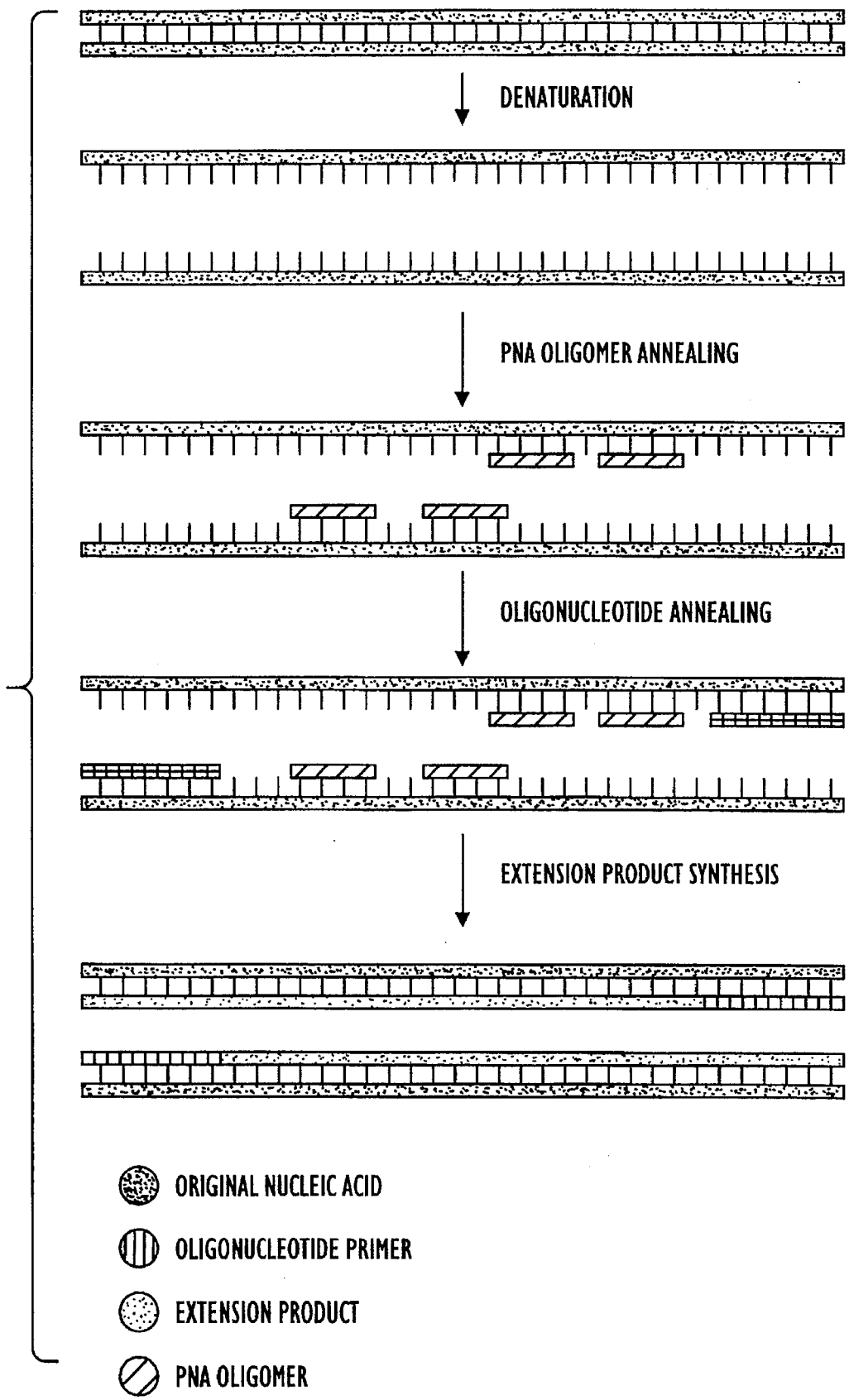
FIG. 4 provides a schematic illustration of the PNA-enhanced polymerase chain reaction.

In the PNA-enhanced PCR reaction, as illustrated in FIG. 4, a DNA sequence of interest is placed in solution with two oligonucleotide primers, one oligonucleotide primer for each strand of each nucleic acid sequence of interest, one or more PNA oligomers which bind within the region of nucleic acid to be amplified but in a position different from that which the oligonucleotide primers bind, a polymerase, and a mixture of four nucleoside triphosphates, deoxyadenosine triphosphate deoxythymidine triphosphate, deoxyguanosine triphosphate, and deoxycytidine triphosphate. The mixture is heated to denature the double-stranded nucleic acid. Such denaturing can be achieved thermally, usually at a temperature of 80° to 100° C., preferably 95°±5° C. It is not necessary to maintain the mixture at the denaturing temperature for any significant length of time. Indeed, in one embodiment of the present invention, the mixture merely reaches the denaturing temperature range and then it is cooled to the PNA oligomer annealing temperature range. Accordingly, a suitable length of time for maintaining this temperature is between an instantaneous period of time and 10 minutes.

The mixture is cooled to allow the one or more PNA oligomers to anneal. The PNA annealing step can occur at any temperature between the denaturing temperature of the double-stranded DNA and the primer annealing temperature. A suitable temperature for the PNA annealing step is a range of from about 70° to 80° C., preferably 72° to 78° C. It is not necessary to maintain the mixture at the PNA annealing temperature for any significant length of time. Indeed, in one embodiment of the present invention, the mixture merely passes through the PNA annealing temperature range as it is cooled to the primer annealing temperature range. Accordingly, a suitable range of time for maintaining the PNA annealing temperature is from an instantaneous period of time up to ten minutes.

The mixture is then brought to a temperature at which the oligonucleotide primers anneal to the DNA template and an extension product from the primers using the nucleic acid sequence as a template is synthesized. A suitable temperature for the for the primer annealing and primer extension product synthesis step is 40° to 80° C. The mixture is maintained at the primer annealing and primer extension product synthesis step for a period of time ranging from an instantaneous period of time to 30 minutes.

These steps constitute one cycle of the PNA-enhanced PCR reaction. To initiate the next cycle, the resultant product of the reaction, two double-stranded DNA molecules, are denatured as in the first step of this cycle.

In a preferred embodiment of the present invention, the oligonucleotide annealing step and the extension product synthesis step are carried out at two separate temperature ranges. The mixture resulting from annealing of the at least one PNA oligomer is brought to a temperature at which the oligonucleotide primers anneal to the DNA template. A suitable temperature for the primer annealing step is 40° to 72° C. The mixture is maintained at the primer annealing temperature for a period of time ranging from an instantaneous period of time to 5 minutes.

After the primers have annealed to the DNA templates, the mixture is heated to the primer extension product synthesis temperature. Preferably, this primer extension product synthesis temperature ranges from 60°–80° C. The mixture is maintained at the primer extension product synthesis temperature for a period of time ranging from an instantaneous period of time to 10 minutes.

It is postulated that, upon denaturation of the double-stranded DNA sequence of interest and cooling to the PNA annealing temperature, the one or more PNA oligomers bind to the complementary regions of the DNA at a region of the nucleic acid sequence which is different from those regions to which the oligonucleotide primers bind. This binding of the one or more PNA oligomers diminishes or eliminates the annealing of the DNA, either internally with a self-complementary region or externally with a complementary strand of DNA. Upon further cooling to the oligonucleotide primer annealing temperature, the primers bind to the DNA templates. Because the PNA oligomers bind to different sites than those to which the oligonucleotide primers bind, the PNA annealing does not interfere with primer annealing.

Upon subsequent warming to the polymerization temperature, the primers are extended by a polymerase. This extension of the primer results in displacement of the one or more PNA oligomers, allowing the synthesis of an extension product through the region to which the one or more PNA oligomers were bound. This displacement of the one or more PNA oligomers during extension of the primer is presumed to result from displacement of the PNA oligomer by the primer extension product, possibly augmented by partial thermal denaturation of the DNA/PNA complex.

The PNAs are synthesized by adaptation of standard peptide synthesis procedures, either in solution or on a solid phase. The synthesis of PNAs is described in Science 254, 1497 (1991); J. Am. Chem. Soc. 114, 9677 (1992); J. Am. Chem. Soc. 144, 1895 (1992); J. Chem. Soc. Chem. Comm. 800 (1993); Proc. Nat. Acad. Sci. USA 90, 1667 (1993); Intercept Ltd. 325 (1992); J. Am. Chem. Soc. 114, 9677 (1992); Nucleic Acids Res. 21, 197 (1993); J. Chem. Soc. Chem. Commun. 518 (1993); Anti-Cancer Drug Design 8, 53 (1993); Nucleic Acids Res. 21, 2103 (1993); Org. Proc. Prep. 25, 457 (1993); CRC Press 363 (1992); J. Chem. Soc. Chem. Commun. 800 (1993); J. Am. Chem. Soc. 115, 6477 (1993); Nature 365, 566 (1993); ABRF News Vol. 4, No. 3 (1993); Science 258, 1481 (1992); WO 8-92/20702; and WO 92/20703, the contents of which are incorporated herein by reference.

The present invention comprises a method using PNA to enhance the efficiency of the PCR amplification of nucleic acid sequences. If present during PCR amplification, PNA allows fragments of different size to be more effectively and more evenly amplified. Differential amplification is less apparent and as a result the risk of misclassification is greatly reduced. In addition, fragments of same or similar size are also amplified more effectively.

The one or more PNA oligomers are selected such that blocking of the nucleic acid template occurs without halting the PCR reaction. The PNA molecule must anneal to the DNA template before the complementary DNA strand. However, it is preferred that the PNA be sufficiently destablized at the primer extension temperature to allow the polymerase to dislodge it and extend through to the end of the template.

The term "PNA oligomer" as used herein is defined as a molecule comprised of two or more PNA monomers. Its exact size will depend on many factors, which in turn depend on the ultimate function or use of the PNA oligomer. In one preferred embodiment of the present invention, the PNA oligomer comprises 5–20 PNA monomers, and more preferably 8–16 PNA monomer units.

Additionally, the sequence of the PNA oligomer is designed to be substantially complementary to a nucleic acid sequence. This means that the one or more PNA oligomers must be sufficiently complementary as to anneal with their respective complementary strands. Therefore, the sequence of PNA oligomer need not reflect the exact sequence of the template. Non-complementary bases or longer sequences can be interspersed in the sequence, provided that the sequence has sufficient complementarity with the sequence of the strand to be amplified to hybridize therewith. Within the context of a preferred embodiment, substantial complementarity of a PNA oligomer designates a situation in which there is not more than two mismatches between the nucleobase sequence of the PNA oligomer and the complementary DNA sequence.

The term "oligonucleotide" as used herein in referring to primers is defined as a molecule comprised of two or more deoxyribonucleotides or ribonucleotides, preferably more than three. Its exact size will depend on many factors, which in turn depend on the ultimate function or use of the oligonucleotide.

The term "primer" as used herein refers to an oligonucleotide, whether occurring naturally as in a purified restriction digest or produced synthetically, which is capable of acting as a point of initiation of synthesis when placed in conditions such that synthesis of a primer extension product which is complementary to a nucleic acid strand is induced, i.e., in the presence of nucleotides and an agent for polymerization, such as a DNA polymerase, and at a suitable temperature and pH. The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and the source of the primer. For example, depending on the complexity of the target sequence, the oligonucleotide primer typically contains 15-25 or more nucleotides, although it may contain fewer nucleotides. Short primer molecules generally require cooler temperatures to form sufficiently stable complexes with the template.

The primers are selected to be "substantially" complementary to one or both strands of each specific sequence to be amplified. This means that the primers must be sufficiently complementary to anneal with their respective strands. Therefore, the sequence need not reflect the exact sequence of the template. For example, a non-complementary nucleotide fragment may be attached to the 5' end with the remainder of the sequence being complementary to the strand. Alternatively, non-complementary bases or longer sequences can be interspersed in the sequence, provided that the sequence has sufficient complementarity with the sequence of the strand to be amplified to hybridize therewith and thereby form a template for synthesis of the extension product of the other primer.

As used herein, the terms "restriction endonucleases" and "restriction enzymes" refer to bacterial enzymes each of which cut double-stranded DNA at or near a specific nucleotide sequence.

As used herein, the term "DNA polymorphism" refers to the condition in which two or more different nucleotide sequences coexist in the same interbreeding population in a DNA sequence.

The present invention is directed to a process for amplifying one or more desired specific nucleic acid sequences suspected of being in a nucleic acid. Because large amounts of a specific sequence may be produced by this process, the present invention may be used for improving the efficiency of cloning DNA or messenger RNA and for amplifying a target sequence to facilitate detection thereof.

In general, the present process involves a chain reaction for producing, in exponential quantities relative to the number of reaction steps involved, at least one specific nucleic acid sequence given that the ends of the required sequence are known in sufficient detail that oligonucleotide primers can be synthesized which will anneal to the ends, and that at least a portion of the sequence different from the ends to which the primers bind is known in sufficient detail that one or more PNA oligomers can be synthesized which will anneal to the sequence. The product of the chain reaction will be a discrete nucleic acid duplex with termini corresponding to the ends of the specific primers employed.

Any source of nucleic acid, in purified or nonpurified form, can be utilized as the starting nucleic acid or acids, provided it is suspected of containing the specific nucleic acid sequence desired. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules.

The nucleic acid or acids may be obtained from any source, for example, from plasmids such as pBR322, from cloned DNA or RNA, or from natural DNA or RNA from any source, including bacteria, yeast, viruses, and higher organisms, such as plants or animals. DNA or RNA may be extracted from blood or tissue material, such as chorionic villi or amniotic cells, by a variety of techniques such as that described by Maniatis et al., Molecular Cloning: A Laboratory Manual, (New York: Cold Spring Harbor Laboratory, 1982), pp. 280-281.

Any specific nucleic acid sequence can be produced by the present process. It is only necessary that a sufficient number of bases at both ends of the sequence and at some point intermediate to the two ends of the sequence be known in sufficient detail so that two oligonucleotide primers and one or more PNA oligomers can be prepared which will anneal to the strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence and at the intermediate point, the greater can be the specificity of the primers and the PNA oligomers for the target nucleic acid sequence, and thus the greater the efficiency of the process.

It will be understood that the word oligonucleotide primer and PNA oligomer as used hereinafter may refer to more than one oligonucleotide primer or PNA oligomer, particularly in the case where there is some ambiguity in the information regarding the terminal sequences or intermediate sequence of the fragment to be amplified. For instance, in the case where a nucleic acid sequence is inferred from protein sequence information a collection of primers and oligomers containing sequences representing all possible codon variations based on degeneracy of the genetic code will be used for each strand.

The oligonucleotide primers may be prepared using any suitable method, such as, for example, the phosphotriester and phosphodiester methods described above, or automated embodiments thereof. In one such automated embodiment, diethylphosphoramidites are used as starting materials and may be synthesized as described by Beaucage et al., Tetrahedron Letters 22, 1859-1862 (1981). One method for synthesizing oligonucleotides on a modified solid support is described in U.S. Pat. No. 4,458,066. It is also possible to use a primer which has been isolated from a biological source, such as a restriction endonuclease digest.

The specific nucleic acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical or enzymatic means. One physical method of separating the strands of the nucleic acid involves heating the nucleic acid until it is completely (>99%) denatured. Typical heat denaturation may involve temperature ranging from about 80° to 100° C. for times ranging from an instantaneous period of time to 10 minutes. Strand separation may also be induced by an enzyme from the class of enzymes known as helicases or the enzyme RecA, which has helicase activity and is known, in the presence of riboATP, to denature DNA. The reaction conditions suitable for separating the strands of nucleic acids with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67, and techniques for using RecA are reviewed in C. Radding, Ann. Rev. Genetics, 16:405–37 (1982).

Preferably, a molar excess, usually about $10^{14}$:1 primer::template of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

If the original nucleic acid containing the sequence to be amplified is single-stranded, its complement is synthesized by adding one or two oligonucleotide primers thereto. If an appropriate single primer is added, a primer extension product is synthesized in the presence of the primer, an agent for polymerization and the four nucleotides described below. The product will be partially complementary to the single-stranded nucleic acid and will anneal with the nucleic acid strand to form a duplex of unequal length strands which may then be separated into single strands as described above to produce two single separated complementary strands. Alternatively, two appropriate primers may be added to the single-stranded nucleic acid and the reaction carried out.

If the original nucleic acid constitutes the sequence to be amplified, the primer extension products produced will be completely complementary to the strands of the original nucleic acid and will anneal therewith to form a duplex of equal length strands to be separated into single-stranded molecules.

Preferably, a molar excess, usually about $10^{14}$:1 primer::template of the PNA oligomer is added to the buffer containing the template. It is understood, however, that the amount of complementary strand may not be known if the process herein is used for diagnostic applications, so that the amount of PNA oligomer relative to the amount of complementary strand cannot be determined with certainty. As a practical matter, however, the amount of PNA oligomer added will generally be in molar excess over the amount of complementary strand (template) when the sequence to be amplified is contained in a mixture of complicated long-chain nucleic acid strands. A large molar excess is preferred to improve the efficiency of the process.

When the complementary strands of the nucleic acid or acids are separated, whether the nucleic acid was originally double or single-stranded, the strands are ready to be used as a template for the synthesis of additional nucleic acid strands. This synthesis can be performed using any suitable method. Generally it occurs in a buffered aqueous solution, preferably at a pH of 7–9, most preferably about 8.

The deoxyribonucleoside triphosphates dATP, dCTP, dGTP and TTP are also added to the synthesis mixture in adequate amounts and the resulting solution is heated to about 90°–100° C. for from an instaneous period of time to 10 minutes, preferably from 1 to 4 minutes. After this heating period the solution is allowed to cool to from 40°–80° C., which is preferable for the primer hybridization. To the cooled mixture is added an agent for polymerization, and the reaction is allowed to occur under conditions known in the art. This synthesis reaction may occur at from room temperature up to a temperature above which the agent for polymerization no longer functions efficiently. Thus, for example, if heat-stable DNA polymerase is used as the agent for polymerization, the temperature is generally no greater than about 72° C.

The agent for polymerization may be any compound or system which will function to accomplish the synthesis of primer extension products, including enzymes. Suitable enzymes for this purpose include, for example, Taq polymerase, AMPLITAQ DNA polymerase (available from Perkin Elmer-Cetus), E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' to 3' direction along the template strand, until synthesis terminates, producing molecules of different lengths. There may be agents, however, which initiate synthesis at the 5' end and proceed in the other direction, using the same process as described above.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional agent for polymerization, nucleotides, PNA oligomers, and oligonucleotide primers may be added, if necessary, for the reaction to proceed under the conditions prescribed above. Again, the synthesis will be initiated at one end of the oligonucleotide primer and will proceed along the single strands of the template to produce additional nucleic acid. After this step, half of the extension product will consist of the specific nucleic acid sequence bounded by the two primers.

The steps of strand separation, PNA oligomer annealing, oligonucleotide primer annealing, and extension product synthesis can be repeated as often as needed to produce the desired quantity of the desired nucleic acid sequence. The amount of the nucleic acid sequence produced will accumulate in an exponential fashion.

When it is desired to produce more than one nucleic acid sequence from the first nucleic acid or mixture of nucleic acids, the appropriate number of different oligonucleotide primers and PNA oligomers are utilized. For example, if two different specific nucleic acid sequences are to be produced, four primers and two or more PNA oligomers are utilized. Two of the primers are specific for one of the nucleic acid sequences and the other two primers are specific for the second nucleic acid sequence. At least one of the PNA oligomers is specific for each nucleic acid sequence. In this manner, each of the two different specific sequences can be produced exponentially by the present process.

The present invention can be performed in a step-wise fashion, where after each step new reagents are added, or simultaneously, where all reagents are added at the initial step, or partially step-wise and partially simultaneous, where fresh reagent is added after a given number of steps. If a method of strand separation, such as heat, is employed which will inactivate the agent for polymerization, as in the case of a heat-labile enzyme, then it is necessary to replenish the agent for polymerization after every strand separation step. The simultaneous method may be utilized when a number of purified components, including an enzymatic means such as helicase, is used for the strand separation step. In the simultaneous procedure, the reaction mixture may contain, in addition to the nucleic acid strand(s) containing the desired sequence, the strand-separating enzyme (e.g., helicase), an appropriate energy source for the strand-separating enzyme, such as ATP, the four nucleotides, the oligonucleotide primers in molar excess, the PNA oligomers in molar excess, and the inducing agent, e.g., Taq polymerase or the Klenow fragment of $E.$ $coli$ DNA polymerase I. If heat is used for denaturation in a simultaneous process, a heat-stable inducing agent such as a thermostable polymerase may be employed which will operate at an elevated temperature, preferably 65°–80° C., depending on the inducing agent, at which temperature the nucleic acid will consist of single and double strands in equilibrium. The upper temperature will depend on the temperature at which the enzyme will degrade or the temperature above which an insufficient level of primer hybridization will occur. Each step of the process will occur sequentially, notwithstanding the initial presence of all the reagents. Additional materials may be added as necessary. After the appropriate length of time has passed to produce the desired amount of the specific nucleic acid sequence, the reaction may be halted by inactivating the enzymes in any known manner or by separating the components of the reaction.

The process of the present invention may be conducted continuously. In one embodiment of an automated process, the reaction may be cycled through a denaturing region, a PNA oligomer reagent addition region, an oligonucleotide primer reagent addition region, and a reaction region. In another embodiment, the enzyme used for the synthesis of primer extension products can be immobilized in a column. The other reaction components can be continuously circulated by a pump through the column and a heating coil in series; thus the nucleic acids produced can be repeatedly denatured without inactivating the enzyme.

The steps of this process can be repeated indefinitely, being limited only by the amount of the oligonucleotide primers, the one or more PNA oligomers, the agent for polymerization and nucleotides present. For detection, the number of cycles used is that required to produce a detectable amount, an amount which will depend, e.g., on the nature of the sample. For example, if the sample is pure, fewer cycles may be required than if it is a complex mixture. If the sample is human genomic DNA, preferably the number of cycles is from about 10–30.

The amount of original nucleic acid remains constant in the entire process, because it is not replicated. The amount of the long products increases linearly because they are produced only from the original nucleic acid. The amount of the specific sequence increases exponentially. Thus, the specific sequence will become the predominant species.

When a single-stranded nucleic acid is utilized as the template, only one long product is formed per cycle.

The method herein may be utilized to clone a particular nucleic acid sequence for insertion into a suitable expression vector. The vector may then be used to transform an appropriate host organism to produce the gene product of the sequence by standard method of recombinant DNA technology.

The amplification process herein may yield a mixture of nucleic acids, resulting from the original template nucleic acid, the expected target amplified products, and various background non-target products. The amplified product can also be a mixture, if the original template DNA contains multiple target sequences, such as in a heterozygous diploid genome or when there is a family of related genes.

The primers herein may be modified to assist the rapid and specific cloning of the mixture of DNAs produced by the amplification reaction. In such modification the same or different restriction sites are incorporated at the 5' ends of the primers to result in restriction sites at the two ends of the amplified product. When cut with the appropriate enzymes, the amplified product can then be easily inserted into plasmid or viral vectors and cloned. This cloning allows the analysis or expression of individual amplified products, not a mixture.

Although the same restriction site can be used for both primers, the use of different sites allows the insertion of the product into the vector with a specific orientation and suppresses multiple insertions as well as insertions arising from amplifications based on only one of the two primers. The specific orientation is useful when cloning into single strand sequencing vectors, when single strand hybridization probes are used, or when the cloned product is being expressed.

One method to prepare the primers is to choose a primer sequence which differs minimally from the target sequence. Regions in which each of the primers is to be located are screened for homology to restriction sites appropriate to the desired vector. For example, the target sequence "CAGTATCCGA..." (SEQ ID NO:1) differs by only one base from one containing a BamHI site. A primer sequence is chosen to match the target exactly at its 3' end, and to contain the altered sequence and restriction site near its 5' end (for example, "CAGgATCCGA..", (SEQ ID NO:2) where the lower case letter symbolizes a mismatch with the target sequence). This minimally altered sequence will not interfere with the ability of the primer to hybridize to the original target sequence and to initiate polymerization. After the first amplification cycle the primer is copied, becomes the target, and matches exactly with new primers. After the amplification process, the products are cleaved with the appropriate restriction enzymes, optionally separated from inhibitors of ligation, such as the nucleoside triphosphates and salts, by passing over a desalting column or molecular weight chromatography column, and inserted by ligation into a cloning vector such as bacteriophage M13. The gene may then be sequenced and/or expressed using well known techniques.

The second method for preparing the primers involves taking the 3' end of the primers from the target sequence and adding the desired restriction site(s) to the 5' end of the primer. For the above example, a HindIII site could be added to make the sequence "cgaagcttCAGTATCCGA...", (SEQ ID NO:3) where lower case letters are as described above. The added bases would not contribute to the hybridization in the first cycle of amplification, but would match in subsequent cycles. The final amplified products are then cut with one or more restriction enzymes and cloned and expressed as described above. The gene being amplified may be, for example, human beta-hemoglobin or the human HLA DQ, DR or DP-alpha and -beta genes.

In addition, the process herein can be used for in vitro mutagenesis. The oligodeoxyribonucleotide primers need not be exactly complementary to the DNA sequence which is being amplified. It is only necessary that they be able to hybridize to the sequence sufficiently well to be extended by the polymerase enzyme or by whatever other inducing agent is employed. The product of a polymerase chain reaction wherein the primers employed are not exactly complementary to the original template will contain the sequence of the primer rather than the template, thereby introducing an in vitro mutation. In further cycles, this mutation will be amplified with undiminished efficiency because no further mispaired primings are required. The mutant thus produced may be inserted into an appropriate vector by standard molecular biological techniques and might confer mutant properties on this vector such as the potential for production of an altered protein.

The process of making an altered DNA sequence as described above could be repeated on the altered DNA using different primers so as to induce further sequence changes. In this way a series of mutated sequences could gradually be produced wherein each new addition to the series could differ from the last in a minor way, but from the original DNA source sequence in an increasingly major way. In this manner changes could be made ultimately which were not feasible in a single step due to the inability of a very seriously mismatched primer to function.

In addition, the primer can contain as part of its sequence a non-complementary sequence, provided that a sufficient amount of the primer contains a sequence which is complementary to the strand to be amplified. For example, a nucleotide sequence which is not complementary to the template sequence (such as, e.g., a promoter, linker, coding sequence, etc.) may be attached at the 5' end of one or both of the primers, and thereby appended to the product of the amplification process. After the extension primer is added, sufficient cycles are run to achieve the desired amount of new template containing the non-complementary nucleotide insert. This allows production of large quantities of the combined fragments in a relatively short period of time (e.g., two hours or less) using a simple technique.

If restriction site linkers are incorporated into the primers, then the amplified double-stranded products can be digested with the appropriate restriction enzymes and ligated directly into a vector for rapid cloning and sequencing. The plaques containing the specific amplified target sequences can be identified by hybridizing plaque lift filters with a probe specific for the target sequence.

The method herein may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells or chorionic villi. Amplification is particularly useful if such an analysis is to be done on a small sample using non-radioactive detection techniques which may be inherently insensitive, or where radioactive techniques are being employed but where rapid detection is desirable.

For purposes of this invention genetic diseases may include specific deletions and/or mutations in genomic DNA from any organism, such as, e.g., sickle cell anemia, cystic fibrosis, alpha-thalassemia, beta-thalassemia, and the like. Sickle cell anemia can be readily detected via a RFLP-like analysis following amplification of the appropriate DNA sequence by the present method. Alpha-thalassemia can be detected by the absence of a sequence, and beta-thalassemia can be detected by the presence of a polymorphic restriction site closely linked to a mutation which causes the disease.

All of these genetic diseases may be detected by amplifying the appropriate sequence and analyzing it. In such a process, for example, a small sample of DNA from biological material, e.g., amniotic fluid or chorionic villi containing a very low level of the desired sequence is amplified, cut with a restriction enzyme, and analyzed.

In another embodiment a small sample of DNA may be amplified to a convenient level and then a further cycle of extension reactions performed wherein nucleotide derivatives which are readily detectable (such as $^{32}$P-labeled or biotin-labeled nucleoside triphosphates) are incorporated directly into the final DNA product, which may be analyzed by restriction and electrophoretic separation or any other appropriate method.

In a further embodiment, the nucleic acid may be exposed to a particular restriction endonuclease prior to amplification. Since a sequence which has been cut cannot be amplified, the appearance of an amplified fragment, despite prior restriction of the DNA sample, implies the absence of a site for the endonuclease within the amplified sequence. The presence or absence of an amplified sequence can be detected by an appropriate method.

In addition to detecting infectious diseases and pathological abnormalities in the genome of organisms, the process herein can also be used to detect DNA polymorphisms.

In a preferred embodiment of the present invention, the nucleic acid sequence which is to be amplified contains at least one sequence portion which is substantially repeated at least once within the nucleic acid sequence. This substantial repetition encompasses both repetition of identical sequence portions and repetition of nearly-identical sequence portions. Nearly-identical portions are those portions which have 80% or greater sequence homology in a given region.

In another preferred embodiment of the present invention, the PNA oligomer forms a duplex with a portion of the nucleic acid sequence of interest, which duplex has a melting temperature within the range of 70°–80° C., preferably 74°–78° C. If the nucleic acid sequence of interest contains a sequence portion which is substantially repeated, then, in a preferred embodiment, the PNA oligomer may be a mixture of several PNA oligomers, each of which is substantially complementary to one or more of the identical or nearly-identical sequence portions.

In still another preferred embodiment of the present invention, the PNA oligomer may be a pair of PNA oligomers, at least a portion of the sequence of each being complementary to the other member of the pair.

Other features of the invention will become apparent in the course of the following descriptions of exemplary embodiments which are given for illustration of the invention and are not intended to be limiting thereof.

The PNA H-CCT(G/T) CCGGTGGTC(C/T)TC-NH2, a composite of four PNA oligomers, was synthesized and provided by Biosearch Division of PerSeptive Biosytems. Bedford, Mass. Oligonucleotide primers used in the PCR reactions were synthesized by Research Genetics (Huntsville, Ala.). The sequences of the primers were 5'-GAAACTGGCCTCCAAACACTCCCCGCCG-3' (forward primer) (SEQ ID NO:4), and 5'-GTCTTGTTGGAGATGCACGTGCCCCTTGC-3' (reverse primer)(SEQ ID NO:5). The forward primer was end-labeled with T4 polynucleotide kinase and γ-$^{32}$P-ATP.

DNA was extracted from EDTA anticoagulated whole blood using a PureGene DNA Isolation Kit (Gentra Systems, Minneapolis, Minn.). Purified DNA from cell line K562 was purchased from Promega Corporation (Madison, Wis.).

Amplification of the D1S80 locus was carried out in a total volume of 12.5 μl using 5 ng of genomic DNA. Each reaction contained 0.75 μM of each primer, 250 μM each of dCTP, dATP, dGTP, and TTP, and 1X Strategene buffer (10 mM Tris-HCl [pH 8.8], 50 mM KCl, 1.5 mM $MgCl_2$, and 0.01% (w/v) gelatin, and other stabilizers not specified). The PCR reactions were overlaid with 1 drop of mineral oil prior to addition of 0.5 units of Stratagene Taq polymerase (La Jolla, Calif.), the reaction mixtures were heated to 95° C. for 4–10 minutes in a GTC-2 Genetic Thermal Cycler (Precision Scientific, Chicago, Ill.). Subsequently, 5 cycles were carried out each consisting of 95° C. for 1.25 minutes for denaturation, 67° C. for 30 seconds to allow primer annealing, and 4 minutes at 72°–76° C. for primer extension, followed by 25 cycles each consisting of 95° C. for 1.25 minutes, 66° C. for 30 seconds, and 72°–76° C. for 4 minutes. The final extension was carried out for an additional 5 minutes.

Electrophoresis of the amplified DNA was carried out on 5% Long Ranger denaturing gel (J. T. Baker) at 1000 V for 3.5 hr. Following electrophoresis, the polyacrylamide gels were dried using a Savant Slab Gel Dryer (Savant, Inc.). The amplification products were visualized by autoradiography using Kodak XAR5 film and Biotech L-Plus intensifying screens (Fisher Scientific).

Figure 5:
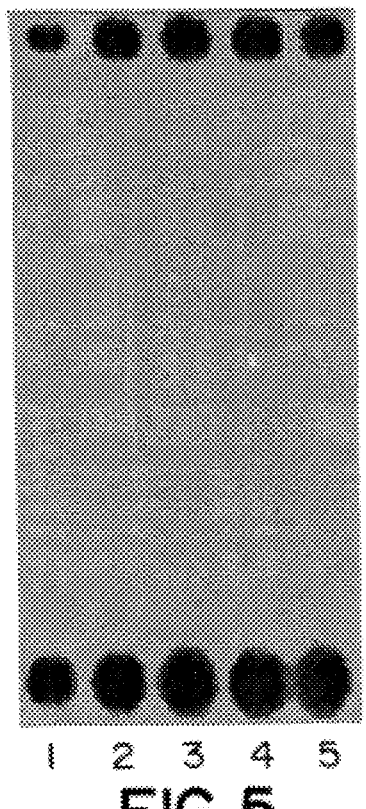
FIG. 5 is an autoradiograph illustrating the results of a polymerase chain reaction obtained in the absence of a PNA oligomer and with varying concentrations of a PNA oligomer.

FIG. 5 is an autoradiograph illustrating the results of the polymerase chain reaction obtained in the absence of PNA oligomers and in the presence of varying amounts of PNA oligomers. Lane 1 represents the reaction detailed above run in the absence of the four PNA oligomers. Lanes 2 to 5 represent the above reaction run in the presence of the four PNA oligomers at concentrations of 0.9 μM, 1.2 μM, 1.5 μM, and 1.8 μM, respectively. As is evidenced in the autoradiograph, in the absence of PNA oligomers (Lane 1), differential amplification does occur. The smaller allele, located at the bottom half of Lane 1 of the autoradiograph, is much more strongly represented relative to the larger allele found in the top half of Lane 1. This differential amplification can result in an erroneous analysis of the sample. In contrast, Lanes 2 to 5, which utilize different concentrations of the PNA oligomers, evidence a much reduced differential amplification.

Figure 6:
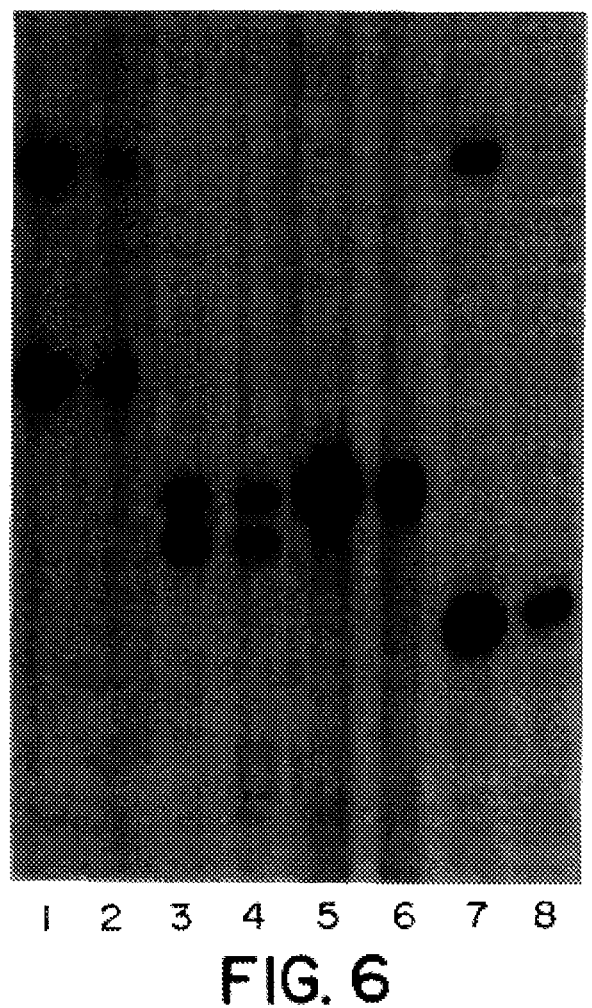
FIG. 6 is an autoradiograph illustrating the results of the PNA-enhanced polymerase chain reaction and the conventional PCR run with various samples of DNA.

To evaluate the general application of PNA for enhancing PCR at the D1S80 locus, 4 DNA specimens from routine paternity casework were randomly selected. Each was amplified with PNA (1.5 μM) and without PNA. All samples were prepared together from the same master mix of reagents and cycled together in the same thermal cycler. Primer extension was carried out at 76° C. The results are shown in FIG. 6. Lanes 1, 3, 5, and 7 represent polymerase chain reaction run in the presence of PNA, while Lanes 2, 4, 6, and 8 represent experiments run in the absence of PNA. Each DNA specimen run with PNA demonstrated enhanced amplification, particularly of the larger allele.

A PNA can be designed to be shorter than the repeat so as to intentionally create gaps and allow read through by the polymerase. A shortened PNA might be useful for enhancing the amplification of loci consisting of conserved repeats.

The foregoing description of preferred embodiments of the invention has been presented for purposes of illustration and description. It is not intended to be exhaustive or to limit the invention to the precise forms disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A process for amplifying a nucleic acid sequence of interest which is in a sample containing at least one nucleic acid molecule, comprising the steps of:

treating the sample by including at least one PNA oligomer which binds within the nucleic acid sequence to be amplified and a polymerase; and amplifying a nucleic acid sequence which is complementary to the nucleic acid sequence of interest.

2. The process according to claim 1 wherein said step of amplifying comprises:

annealing at least one oligonucleotide primer to said nucleic acid sequence of interest and extending the at least one oligonucleotide primer so as to synthesize at least one extension product employing said nucleic acid sequence as a template wherein the at least one PNA oligomer is displaced from the template during the synthesis of the extension product.

3. The process according to claim 2, wherein said nucleic acid sequence of interest includes a sequence portion which is substantially repeated at least once within the nucleic acid sequence of interest.

4. The process according to claim 3, wherein the at least one PNA oligomer comprises a mixture of several PNA oligomers, each of which is substantially complementary to a portion of said nucleic acid sequence of interest.

5. The process according to claim 2, wherein said nucleic acid sequence of interest includes a sequence portion which is repeated at least once within the nucleic acid sequence of interest.

6. The process according to claim 2, wherein during the PNA oligomer binding step, said at least one PNA oligomer forms a duplex with a portion of the nucleic acid sequence of interest, said duplex having a melting temperature within the range of 70° C. to 80° C.

7. The process according to claim 6, wherein said duplex has a melting temperature within the range of 74° to 78° C.

8. The process according to claim 2, wherein the at least one PNA oligomer comprises a pair of PNA oligomers at least a portion of the sequence of each of said pair being complementary to the other.

9. The process according to claim 2, wherein said at least one PNA oligomer each comprises 5 to 20 PNA monomers.

10. The process according to claim 9, wherein said at least one PNA oligomer each comprises 8 to 16 PNA monomers.

11. A method of amplifying a nucleic acid sequence of interest in a sample containing at least one nucleic acid molecule, comprising:

(a) treating the sample with
        (i) a polymerase,
        (ii) at least one oligonucleotide primer which binds to the nucleic acid sequence of interest,
        (iii) at least one PNA oligomer which is substantially complementary to a portion of and which binds within the nucleic acid sequence of interest at a position different from the position at which the oligonucleotide primer binds, and
        (iv) four different nucleoside triphospates, forming a first mixture;

(b) heating the first mixture to within a first temperature range so as to denature the nucleic acid and to separate any of the at least one oligonucleotide primer and any of the at least one PNA oligomer which are bound to the nucleic acid, forming a second mixture;

(c) cooling the second mixture to within a second temperature range at which the at least one PNA oligomer binds to the nucleic acid sequence of interest, forming a third mixture;

(d) bringing the third mixture to within a third temperature range at which the at least one oligonucleotide primer binds to the nucleic acid sequence of interest and at which an extension product is synthesized from the oligonucleotide primer on each strand, provided the nucleic acid sequence of interest is present, said synthesis employing the nucleic acid as a template, and whereby the at least one PNA oligomer is displaced from the nucleic acid sequence of interest during said synthesis.

12. The method according to claim 11, comprising repeating steps (b), (c), and (d) at least one time.

13. The method according to claim 11, further comprising the step of
(e) treating the product of step (d) under denaturing conditions to separate the extension product from said template.

14. The method according to claim 13, further comprising the step of
(f) detecting the presence of any of said nucleic acid sequence of interest.

15. The method according to claim 11, wherein the nucleic acid sequence of interest includes a sequence portion which is substantially repeated at least once within the nucleic acid sequence of interest.

16. The method according to claim 15, wherein the at least one PNA oligomer comprises a mixture of several PNA oligomers, each of which is substantially complementary to said sequence portion.

17. The method according to claim 11, wherein said nucleic acid sequence of interest includes a sequence portion which is repeated at least once within the nucleic acid sequence of interest.

18. The method according to claim 11, wherein during step (c) the at least one PNA oligomer forms a duplex with a portion of the nucleic acid sequence of interest, said duplex having a melting temperature within the range of 70° to 80° C.

19. The method according to claim 18, wherein said duplex has a melting temperature within the range of 74° to 78° C.

20. The method according to claim 11, wherein the at least one PNA oligomer comprises a pair of PNA oligomers, at least a portion of the sequence of each of said pair being complementary to the other.

21. The method according to claim 11, wherein the first temperature range is a range of 80° to 100° C.

22. The method according to claim 11, wherein the second temperature range is a range of 70° to 80° C.

23. The method according to claim 22, wherein the second temperature range is a range of 72° to 78° C.

24. The method according to claim 11, wherein the third temperature range is a range of 40° to 80° C.

25. The method according to claim 11, wherein each of said at least one PNA oligomer comprises 5 to 20 PNA monomers.

26. The method according to claim 25, wherein each of said at least one PNA oligomer comprises 8 to 16 PNA monomers.

27. The method according to claim 11, wherein, while performing steps (c) and (d), the temperature is continuously varied.

28. The method according to claim 11, wherein, during each of steps (c) and (d), the temperature is maintained at a substantially constant value for an interval of time.

29. The method according to claim 11, wherein step (d) comprises the steps of:

(d1) bringing the third mixture to within a fourth temperature range which is within said third temperature range and at which the at least one oligonucleotide primer binds to the nucleic acid sequence of interest, forming a fourth mixture;

(d2) heating the fourth mixture to within a fifth temperature range which is within said third temperature range and at which said extension product is synthesized from the oligonucleotide primer on each strand, whereby the at least one PNA oligomer is displaced from the nucleic acid sequence of interest, forming a fifth mixture.

30. The method according to claim 29, comprising repeating steps (b), (c), and (d) at least one time.

31. The method according to claim 29, further comprising the step of
(e) treating the product of step (d) under denaturing conditions to separate the extension product from said template.

32. The method according to claim 31, further comprising the step of
(f) detecting the presence of any of said nucleic acid sequence of interest.

33. The method according to claim 29, wherein the first temperature range is a range of 80° to 100° C.

34. The method according to claim 29, wherein the second temperature range is a range of 70° to 80° C.

35. The method according to claim 34, wherein the second temperature range is a range of 72° to 78° C.

36. The method according to claim 29, wherein the fourth temperature range is a range of 40° to 72° C.

37. The method according to claim 29, wherein the fifth temperature range is a range of 60° to 80° C.

38. The process according to claim 1 using a kit wherein said kit comprises:

a) a container containing at least one oligonucleotide primer for each strand of each nucleic acid sequence of interest, each of said at least one oligonucleotide primer being substantially complementary to a strand of each nucleic acid sequence of interest;

b) a container containing at least one PNA oligomer which is substantially complementary to a portion of and which binds within each nucleic acid sequence of interest at a position different form the position at which the at least one oligonucleotide primer binds; and c) a container containing each of four different nucleoside triphosphates.

39. The process according to claim 38, wherein said kit further comprises:

(d) a container containing an agent for polymerization.

40. The process according to claim 38 wherein said nucleic acid of interest includes a sequence portion which is substantially repeated at least once within the nucleic acid sequence of interest.

41. The process according to claim 40, wherein the at least one PNA oligomer comprises a mixture of several PNA oligomers, each of which is substantially complementary to said sequence portion.

42. The process according to claim 38 wherein said nucleic acid sequence of interest includes a sequence portion which is repeated at least once within the nucleic acid sequence of interest.

43. The process according to claim 38, wherein the at least one PNA oligomer forms a duplex with a portion of the nucleic acid sequence of interest, said duplex having a melting temperature within the range of 70° to 80° C.

44. The process according to claim 43, wherein said duplex has a melting temperature within the range of 74° to 78° C.

45. The process according to claim 38, wherein the at least one PNA oligomer comprises a pair of PNA oligomers, at least a portion of the sequence of each of said pair being complementary to the other.

46. The process according to claim 38, wherein each of said at least one PNA oligomer comprises 5 to 20 PNA monomers.

47. The process according to claim 46, wherein each of said at least one PNA oligomer comprises 8 to 16 PNA monomers.

48. A process for cloning into a vector a nucleic acid sequence of interest in a sample containing at least one nucleic acid, comprising:
   (a) treating the sample with
      i) a polymerase,
      ii) at least one oligonucleotide primer containing a restriction site at its 5' end and which is substantially complementary to and binds to a strand of each different nucleic acid sequence of interest,
      iii) at least one PNA oligomer which is substantially complementary to a portion of and which binds within the nucleic acid sequence of interest at a position different from the position at which the oligonucleotide primer binds, and
      iv) four different nucleoside triphosphates, forming a first mixture;
   (b) heating the first mixture to within a first temperature range so as to denature the nucleic acid and to separate any of the at least one oligonucleotide primer and any of the at least one PNA oligomer which is bound to the nucleic acid, forming a second mixture;
   (c) cooling the second mixture to within a second temperature range at which the at least one PNA oligomer binds to the nucleic acid, forming a third mixture;
   (d) bringing the third mixture to within a third temperature range at which the at least one oligonucleotide primer binds to the nucleic acid sequence of interest and at which an extension product is synthesized from the oligonucleotide primer on each strand, provided the nucleic acid sequence of interest is present, said synthesis employing the nucleic acid as a template, and whereby the at least one PNA oligomer is displaced from the nucleic acid sequence of interest during said synthesis
   (e) adding to the product of step (d) a restriction enzyme which cleaves at said restriction site to thereby obtain cleaved products; and
   (f) ligating the cleaved products into at least one cloning vector.

49. The process according to claim 48, comprising repeating steps (b), (c), and (d) at least one time.

50. The process according to claim 48, wherein said nucleic acid sequence of interest includes a sequence portion which is substantially repeated at least once within the nucleic acid sequence of interest.

51. The process according to claim 50, wherein the at least one PNA oligomer comprises a mixture of several PNA oligomers, each of which is substantially complementary to said sequence portion.

52. The process according to claim 48, wherein said nucleic acid sequence of interest includes a sequence portion which is repeated at least once within the nucleic acid sequence of interest.

53. The process according to claim 48, wherein during step (c) the at least one PNA oligomer forms a duplex with a portion of the nucleic acid sequence of interest, said duplex having a melting temperature within the range of 70° to 80° C.

54. The process according to claim 53, wherein said duplex has a melting temperature within the range of 74° to 78° C.

55. The process according to claim 48, wherein the at least one PNA oligomer comprises a pair of PNA oligomers, at least a portion of the sequence of each of said pair being complementary to the other.

56. The process according to claim 48, wherein the first temperature range is a range of 80° to 100° C.

57. The process according to claim 48, wherein the second temperature range is a range of 70° to 80° C.

58. The process according to claim 57, wherein the second temperature range is a range of 72° to 78° C.

59. The process according to claim 48, wherein the third temperature range is a range of 40° to 80° C.

60. The process according to claim 48, wherein each of said at least one PNA oligomer comprises 5 to 20 PNA monomers.

61. The process according to claim 60, wherein each of said at least one PNA oligomer comprises 8 to 16 PNA monomers.

62. The process according to claim 48, wherein, while performing steps (c) and (d), the temperature is continuously varied.

63. The process according to claim 48, wherein, during each of steps (c) and (d), the temperature is maintained at a substantially constant value for an interval of time.

64. The process according to claim 48, wherein step (d) comprises the steps of:
   (di) bringing the third mixture to within a fourth temperature range which is within said third temperature range and at which the at least one oligonucleotide primer binds to the nucleic acid sequence of interest, forming a fourth mixture;
   (dii) heating the fourth mixture to within a fifth temperature range which is within said third temperature range and at which said extension product is synthesized from the oligonucleotide primer on each strand, whereby at least one PNA oligomer is displaced from the nucleic acid sequence of interest, forming a fifth mixture.

65. The process according to claim 64, wherein the first temperature range is a range of 80° to 100° C.

66. The process according to claim 64, wherein the second temperature range is a range of 70° to 80° C.

67. The process according to claim 66, wherein the second temperature range is a range of 72° to 78° C.

68. The process according to claim 64, wherein the fourth temperature range is a range of 40° to 72° C.

69. The process according to claim 64, wherein the fifth temperature range is a range of 60° to 80° C.

70. A solution containing amplified nucleic acid sequences including an amplified nucleic acid sequence of interest wherein said amplified nucleic acid sequences including said amplified nucleic acid sequence of interest have been amplified by an amplification process comprising the steps of:
   a) treating a sample containing nucleic acids with
      i) a polymerase,
      ii) at least one oligonucleotide primer which binds to a strand of said nucleic acid sequence of interest, iii) at least one PNA oligomer which is substantially complementary to and binds within the nucleic acid sequence of interest at a position different from the position at which the at least one oligonucleotide primer binds, and iv) four different nucleoside triphosphates, forming a first mixture;

b) heating the first mixture to within a first temperature range so as to denature the at least one PNA oligomer which is bound to the nucleic acid, forming a second mixture;

c) cooling the second mixture to within a second temperature range at which the at least one PNA oligomer binds to the nucleic acid sequence of interest forming a third mixture;

d) bringing the third mixture to within a third temperature range at which the at least one oligonucleotide primer binds to the nucleic acid sequence of interest and at which an extension product is synthesized from the oligonucleotide primer on each strand, said synthesis employing the nucleic acid as a template, and whereby the at least one PNA oligomer is displaced from the nucleic acid sequence of interest during said synthesis to form said solution of said amplified nucleic acid sequences including an amplified nucleic acid sequence of interest.

71. The solution containing amplified nucleic acid sequences according to claim 70, wherein said amplification process further comprises repeating steps (b), (c), and (d) at least one time.

72. The solution containing amplified nucleic acid sequences according to claim 70, wherein the amplification process further comprises the step of
(e) treating the product of step (d) under denaturing conditions to separate the extension product from said template.

73. The solution containing amplified nucleic acid sequences according to claim 72, wherein the amplification process further comprises the step of
(f) detecting the nucleic acid sequence of interest.

74. The solution containing amplified nucleic acid sequences according to claim 70, wherein in the amplification process said nucleic acid sequence of interest includes a sequence portion which is substantially repeated at least once within the nucleic acid sequence of interest.

75. The solution containing an amplified nucleic acid sequence according to claim 74, wherein the at least one PNA oligomer comprises a mixture of several PNA oligomers, each of which is substantially complementary to said sequence portion.

76. The solution containing amplified nucleic acid sequences according to claim 70, wherein in the amplification process said nucleic acid sequence of interest includes a sequence portion which is repeated at least once within the nucleic acid sequence of interest.

77. The solution containing amplified nucleic acid sequences according to claim 70, wherein during step (c) of the amplification process the at least one PNA oligomer forms a duplex with a portion of the nucleic acid sequence of interest, said duplex having a melting temperature within the range of 70° to 80° C.

78. The solution containing amplified nucleic acid sequences according to claim 77, wherein in the amplification process said duplex has a melting temperature within the range of 74° to 78° C.

79. The solution containing amplified nucleic acid sequences according to claim 70, wherein in the amplification process the at least one PNA oligomer comprises a pair of PNA oligomers, at least a portion of the sequence of each of said pair being complementary to the other.

80. The solution containing amplified nucleic acid sequences according to claim 70, wherein in the amplification process the first temperature range is a range of 80° to 100° C.

81. The solution containing amplified nucleic acid sequences according to claim 70, wherein in the amplification process the second temperature range is a range of 70° to 80° C.

82. The solution containing amplified nucleic acid sequences according to claim 81, wherein in the amplification process the second temperature range is a range of 72° to 78° C.

83. The solution containing amplified nucleic acid sequences according to claim 70, wherein in the amplification process the third temperature range is a range of 40° to 80° C.

84. The solution containing amplified nucleic acid sequences according to claim 70, wherein in the amplification process said at least one PNA oligomer comprises a PNA polymer containing 5 to 20 PNA monomers.

85. The solution containing amplified nucleic acid sequences according to claim 84, wherein in the amplification process said at least one PNA oligomer comprises a PNA polymer containing 8 to 16 PNA monomers.

86. The solution containing amplified nucleic acid sequences according to claim 70, wherein, while performing steps (c) and (d) of the amplification process, the temperature is continuously varied.

87. The solution containing amplified nucleic acid sequences according to claim 70, wherein, during each of steps (c) and (d) of the amplification process, the temperature is maintained at a substantially constant value for an interval of time.

88. The solution containing amplified nucleic acid sequences according to claim 70, wherein step (d) of the amplification process comprises the steps of:
(di) bringing the third mixture to within a fourth temperature range which is within said third temperature range and at which the at least one oligonucleotide primer binds to the nucleic acid sequence of interest, forming a fourth mixture;
(dii) heating the fourth mixture to within a fifth temperature range which is within said third temperature range and at which said extension product is synthesized from the oligonucleotide primer on each strand, whereby the at least one PNA oligomer is displaced from the nucleic acid sequence of interest, forming a fifth mixture.

89. The solution containing an amplified nucleic acid sequences according to claim 88, wherein the defined process further comprises repeating steps (b), (c), and (d) at least one time.

90. The solution containing amplified nucleic acid sequences according to claim 88, wherein the defined process further comprises the step of;
(e) treating the product of step (d) under denaturing conditions to separate the extension product from said template.

91. The solution containing an amplified nucleic acid sequences according to claim 89, wherein the defined process further comprises the step of:
(f) detecting the presence of any of said nucleic acid sequence of interest.

92. The solution containing amplified nucleic acid sequences according to claim 88, wherein in the amplification process the first temperature range is a range of 80° to 100° C.

93. The solution containing amplified nucleic acid sequences according to claim 88, wherein in the amplification process the second temperature range is a range of 70° to 80° C.

94. The solution containing amplified nucleic acid sequences according to claim 93, wherein in the amplification process the second temperature range is a range of 72° to 78° C.

95. The amplified nucleic acid sequence according to claim 88, wherein the fourth temperature range is a range of 40° to 72° C.

96. The solution containing amplified nucleic acid sequences according to claim 88, wherein in the amplification process the fifth temperature range is a range of 60° to 80° C.

97. A method for replicating a target nucleic acid strand with a polymerase to produce a complementary nucleic acid strand of the target nucleic acid strand comprising:
 (a) providing a peptide nucleic acid (PNA) which,
  (i) is substantially complementary in sequence to nucleotides in at least a portion of the target strand,
  (ii) anneals with said portion of the target strand and
 (b) annealing the PNA to the target strand and replicating the target nucleic acid strand with the polymerase to thereby produce the complementary strand of the target nucleic acid strand.

98. The method according to claim 97, wherein step (a) comprises providing a mixture of PNA oligomers, wherein the nucleobase sequence of at least one of the PNA oligomers in the mixture is complementary in sequence to said portion of the target strand.

99. The method according to claim 97, wherein the PNA oligomer provided in step (a) comprises 5 to 20 nucleotides complementary in sequence to said portion of the target strand.

100. The method according to claim 99, wherein the PNA oligomer provided in step (a) comprises 8 to 16 nucleotides complementary in sequence to said portion of the target strand.

101. The method according to claim 97, wherein the target strand comprises, a multiplicity of perfect or imperfect sequence repeats.

102. The method according to claim 97, wherein the polymerase is a DNA polymerase.

103. The method according to claim 102, wherein the DNA polymerase is a thermostable DNA polymerase.

104. The method according to claim 102, further comprising the step of annealing an oligonucleotide primer to a different portion of the target strand thereby to produce a replication initiation site for the polymerase.

105. The method according to claim 103, further comprising the step of annealing an oligonucleotide primer to a different portion of the target strand thereby to produce a replication initiation site for the polymerase.

106. A method for replicating a target nucleic acid strand with a thermostable DNA polymerase to produce a complementary nucleic acid strand of the target nucleic acid strand comprising:
 (a) providing a peptide nucleic acid (PNA) which,
  (i) is substantially complementary in sequence to nucleotides in at least a portion of the target nucleic acid strand,
  (ii) anneals with said portion of the target nucleic acid strand and
  (iii) when annealed with said portion of the target nucleic acid strand, does not serve as a replication initiation site for the polymerase; and
 (b) annealing the PNA to the target nucleic acid strand and replicating the target nucleic acid strand with the polymerase to thereby produce the complementary strand of the target nucleic acid strand.

107. The method according to claim 106, wherein step (a) comprises providing a mixture of PNA oligomers, wherein the nucleobase sequence of at least one of the PNA oligomers in the mixture is complementary in sequence to said portion of the target strand.

108. The method according to claim 106, wherein the PNA oligomer provided in step (a) comprises 5 to 20 nucleotides complementary in sequence to said portion of the target strand.

109. The method according to claim 108, wherein the PNA provided in step (a) comprises 8 to 16 nucleotides complementary in sequence to said portion of the target strand.

110. The method according to claim 106, wherein the target strand comprises a multiplicity of nucleotide sequence repeats.

111. The method according to claim 106, further comprising the step of:
 (C) annealing an oligonucleotide primer to a second nucleobase sequence of the target strand thereby to produce a replication initiation site for the polymerase.

112. A method for replicating a target nucleic acid strand with a polymerase comprising:
 (a) providing a target nucleic acid strand having a multiplicity of nucleotide sequence repeats;
 (b) forming a target nucleic acid strand-PNA oligomer complex by providing a PNA oligomer and annealing said PNA oligomer to the target nucleic acid strand wherein the PNA oligomer is:
  (i) substantially complementary in sequence to at least a portion of one of the repeats;
  (ii) anneals with the at least a portion of one of the repeats thereby to form a target nucleic acid strand-PNA oligomer complex; and
  (iii) when annealed with the at least a portion of the repeats, does not serve as a replication initiation site for the polymerase; and
 (c) incubating the complex in the presence of the polymerase.

113. The method according to claim 112, wherein step (b) comprises providing a mixture of PNA oligomers, wherein the nucleotide sequence of at least one of the PNA oligomers in the mixture is complementary in sequence to said at least a portion of one of the repeats.

114. The method according to claim 112, wherein the PNA oligomer provided in step (b) comprises 5 to 20 nucleotides complementary in sequence to said at least a portion of one of the repeats.

115. The method according to claim 114, wherein the PNA oligomer provided in step (b) comprises 8 to 16 nucleotides complementary in sequence to said at least a portion of one of the repeats.

116. The method according to claim 112, wherein the polymerase is a DNA polymerase.

117. The method according to claim 116, wherein the DNA polymerase is a thermostable DNA polymerase.

118. The method according to claim 112 further comprising the step of:
 (d) annealing a primer to a different portion of the target strand thereby to produce a replication initiation site for the polymerase.

* * * * *